United States Patent [19]

Gold-Aubert et al.

[11] 4,185,104

[45] Jan. 22, 1980

[54] TRANQUILLIZING COMPLEXES

[75] Inventors: Philippe Gold-Aubert; Diran Melkonian, both of Geneva, Switzerland

[73] Assignee: Sapos S.A., Geneva, Switzerland

[21] Appl. No.: 846,370

[22] Filed: Oct. 28, 1977

[30] Foreign Application Priority Data

Nov. 1, 1976 [GB] United Kingdom ............... 45263/76

[51] Int. Cl.² .................. A61K 31/515; C07D 239/62
[52] U.S. Cl. .................................... 424/254; 544/296; 544/301; 544/302
[58] Field of Search ................ 424/254; 260/257; 544/296, 301, 302

[56] References Cited

U.S. PATENT DOCUMENTS 3,075,983  1/1963  Gold-Aubert .................. 424/254

FOREIGN PATENT DOCUMENTS 1193438  6/1970  United Kingdom ............... 260/257

*Primary Examiner*—Paul M. Coughlan, Jr.
*Attorney, Agent, or Firm*—Bacon & Thomas

[57] ABSTRACT

Discrete tetrameric complexes of malonylurea derivatives are described in which the properties expected of the individual malonylurea derivatives are beneficially modified. The complexes are of high purity and are of considerable value in the treatment of alcoholism. Simple processes for preparing the complexes are also disclosed as are compositions containing them.

12 Claims, No Drawings

TRANQUILLIZING COMPLEXES

This invention, of which Philippe Gold-Aubert and Diran Melkonian are the inventors, relates to malonylurea complexes which have a tranquillising effect and more particularly valuable effects in the treatment of tremors.

Many compounds are known which have a sedative and/or tranquillising effect. The best-known include derivatives of malonylurea and these constitute a large class of psychotropic drugs that have been widely used clinically for the treatment of numerous neural disorders, including anxiety states and phychomotor disturbances, whether of emotional, alcoholic, medicinal or mental origin.

Unfortunately, there are several drawbacks attached to the use of this class of drugs which have restricted their use, in some cases quite severely. The class is generally rather unselective in action and many of the drugs have such a wide range of psychotropic properties that it is frequently the case that a drug that is best for the treatment of for example, tremors not only has unwanted sedative or hypnotic side effects, but may even impair consciousness completely at the required dosage levels. In chronic cases there is also the danger of addiction and the requirement for a constantly increasing dose in order to relieve the symptoms, and this may in time prove fatal.

Compounds of this class have generally been administered singly in compositions, but in our British Pat. No. 1,193,438 a composition was disclosed which contained a mixture of three malonylurea derivatives. This mixture was prepared by a single chemical reaction, the resulting mixed product being used directly in the preparation of pharmaceutical compositions. These compositions have properties rather different from the properties that would be predicted from a knowledge of the properties of the individual components and they have proved very valuable in the treatment of a number of complaints of psychotropic origin.

The three-component composition disclosed above was isolated directly from the reaction mixture and this was very convenient, since it obviated the need to separate the individual constituents which was a difficult, uneconomical and time-consuming task; surprisingly the resulting mixture could be obtained in a degree of purity quite acceptable for general pharmaceutical purposes. However, we have since found that a minor amount (less than 5%) of a degradation product is present in the reaction product mixture and the purified product mixture has never been prepared in a form free from such impurities. Crystallisation by way of purification has not been achieved, only vitreous forms of the mixture being obtainable.

We have now been able to prepare a range of complexes which consist of molecules of three malonylurea derivatives linked together so as to form discrete tetrameric entities. These complexes have been found to modify the usual properties of barbiturates very considerably with great therapeutic advantage. In addition, because they may be prepared directly from their constituent molecules, a high degree of purity is obtainable and many of the complexes can be prepared in crystalline or powder form.

According to one aspect of the invention therefore, we provide complexes of the structure

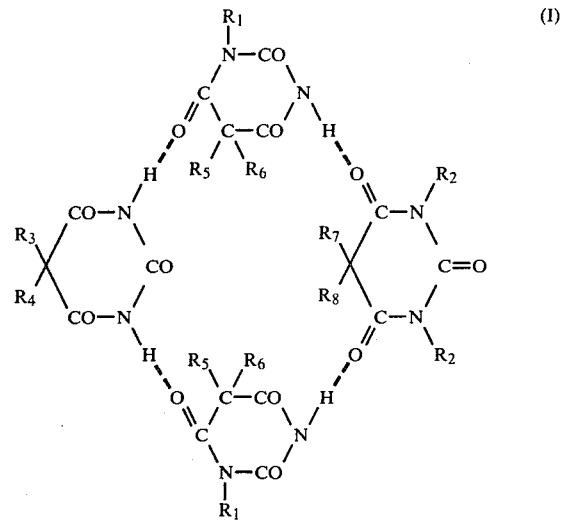

wherein
$R_1$ and $R_2$, which may be the same or different, each represent a group of the formula —$CH_2$ CH A B, in which A may be a hydrogen atom and B a hydroxyl group; or A may be a group having the formula —$CH_2OX$ wherein X is a hydrogen atom or a $C_{1-5}$ alkyl group, and B may be a group of the formula —OY wherein Y is a hydrogen atom or a carbamoyl, substituted carbamoyl or carboalkoxy group; and $R_3$, $R_4$, $R_5$, $R_6$, $R_7$ and $R_8$, which may be the same or different represent hydrogen atoms or aliphatic, araliphatic or aryl groups, the dotted lines representing hydrogen bonding.

Preferred are complexes in which A is a group of the formula —$CH_2OX$ wherein X is a $C_{1-4}$ alkyl group e.g. methyl, ethyl, propyl or butyl; complexes in which B is a group of formula —OY in which Y is a carbamoyl group, and complexes in which $R_3$ to $R_8$ are selected from $C_{2-5}$ alkyl or alkenyl groups, e.g. ethyl, allyl or isopentyl groups, and aryl, e.g. phenyl, groups. Most preferred are complexes in which A is a —$CH_2OX$ group wherein X is an isopropyl or n-butyl group, B is a carbamoyloxy group, and $R_3$ to $R_8$ are selected from ethyl, allyl, isoamyl and phenyl groups.

It is to be emphasised that one major advantage of the tetramers, as compared with the previous three-part reaction mixtures, is that they can be produced in a relatively pure form. In particular all the N,N- unsubstituted malonylurea is bound in the tetramers and its physiological effect thereby modified whereas any N,N- unsubstituted malonylurea in the previous three-part complexes over the stoichiometric quantity required for tetramer formation was not subject to such modification.

The invention further includes complexes of the formula (I) together with a pharmaceutical carrier, diluent or excipient.

The compounds of the invention may be prepared either by
(a) fusing together in molar ratios of 1:2:1 respectively, a malonylurea derivative of formula (II)

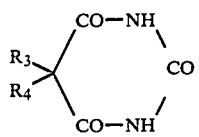

an N-substituted malonylurea derivative of formula (III)

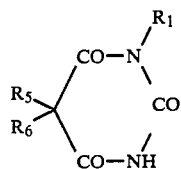

and an N,N-disubstituted malonylurea derivative of formula (IV)

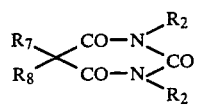

wherein $R_1$ to $R_8$ are as defined above, conveniently followed by treatment of the resulting mixture with cold water and subsequent drying; or (b) by dissolving at moderately elevated temperature compounds of the formulae (II), (III) and (IV) above, in the molar ratio 1:2:1 respectively in alcohol, followed by cooling of the solution and precipitation with water to give an insoluble oil. This oil is then washed in hot water and dried, as in (a) above. This drying is preferably accomplished in vacuo and carried out at constant weight; the residue may then be pulverised to give a white powder.

The compounds of formula (III) and (IV) may be prepared by introducing a group $R_1$ or group $R_2$ on to the unsubstituted nitrogen atom(s) of a compound of formula (II) in which $R_3$ and $R_4$ are identical to $R_5$ and $R_6$ or $R_7$ and $R_8$. This is conveniently effected by reacting an alkali metal derivative of the compound of formula (II) with a compound of the formula $R_1$.Hal or $R_2$.Hal, where Hal is a halogen atom, preferably a chlorine or bromine atom, and $R_1$ and $R_2$ are as hereinbefore defined. The alkali metal is preferably sodium. Reaction may conveniently be performed in an organic solvent, e.g. toluene or an alcohol, or by direct fusion and extended heating. The N-substituted and N,N-disubstituted derivatives may be separated by the action of caustic alkali, e.g. caustic soda, in which the N-substituted derivative is soluble but the N,N-disubstituted derivative is not. Once the compounds have been separated the N,N-disubstituted derivative may be purified by conventional techniques e.g. by precipitation and recrystallisations, when possible, from water and chloroform or petroleum ether respectively. The N-substituted derivative is conveniently precipitated by the action of dilute mineral acid and washed with dilute sodium carbonate to separate the malonylurea compounds that have not reacted. Recrystallisation or reprecipitation from appropriate solvents, e.g. toluene/petroleum ether may then be effected.

Table 1 and Table 2 show the N- and N,N-substituted malonylurea derivatives that we have prepared, some of which are novel compounds.

Table 1

Individual malonylurea derivatives prepared for incorporation into complexes of the invention. Compounds of formula(IV) in which

| $R_7$ $R_8$ | $R_2$ | $R_f$ value | M.Pt. °C. | C% Cald. | C% Found | H% Cald. | H% Found | N% Cald. | N% Found |
|---|---|---|---|---|---|---|---|---|---|
| Ethyl Ethyl | A=—CH$_2$O-n,butyl B=carbamoyloxy | 0.33 | 50.8° | 54.35 | 54.28 | 7.92 | 8.18 | 10.56 | 10.37 |
| n-Propyl n-Propyl | A=—CH$_2$O-n,butyl B carbamoyloxy | 0.45 | Glass | 56.91 | 55.91 | 8.24 | 8.22 | 10.03 | 9.74 |
| Allyl Allyl | A=—CH$_2$O-n,butyl B=carbamoyloxy | 0.47 | Glass | 56.31 | 56.25 | 7.58 | 7.82 | 10.10 | 9.77 |
| Ethyl iso-amyl | A=—CH$_2$O—n,butyl B-carbamoyloxy | 0.55 | 74.1° | 56.64 | 56.83 | 8.39 | 8.72 | 9.79 | 9.54 |
| Ethyl Phenyl | A=—CH$_2$O-n,butyl B-carbamoyloxy | 0.44 | 80°–81° | 58.13 | 58.23 | 7.26 | 7.37 | 9.68 | 9.63 |
| Ethyl Phenyl | A=—CH$_2$O—n,butyl B=OH | 0.60 | Glass | 63.41 | 63.35 | 8.13 | 8.37 | 5.69 | 5.49 |
| Ethyl Phenyl | A=—CH$_2$O-n-butyl B=—CH$_3$ | 0.58 | 132.4° | 60.1 | 60.45 | 6.92 | 6.60 | 10.2 | 10.27 |
| Ethyl Phenyl | A=—CH$_2$—O—CH$_3$ B-carbamoyloxy | 0.13 | 45.8° | 52.83 | 52.97 | 6.07 | 6.38 | 11.33 | 10.85 |
| Ethyl Phenyl | A=—CH$_2$—O—C$_2$H$_5$ B-carbamoyloxy | 0.29 | glass | 55.17 | 55.10 | 6.51 | 6.68 | 10.72 | 10.40 |
| Ethyl Phenyl | A=—CH$_2$—O-n-propyl B=carbamoyloxy | 0.33 | 35.2° | 56.72 | 56.69 | 6.90 | 7.09 | 10.18 | 9.97 |
| Ethyl Phenyl | A=—CH$_2$O—isopropyl B=carbamoyloxy | 0.50 | 147.1° | 56.72 | 56.87 | 6.90 | 7.05 | 10.18 | 10.46 |

Table 2

Compounds of formula (III) in which

| $R_5$-$R_6$ | $R_1$ | $R_f$ value | M.Pt.° C. | C% Cald. | C% Found | H% Cald. | H% Found | N% Cald. | N% Found |
|---|---|---|---|---|---|---|---|---|---|
| Ethyl Ethyl | A=—CH$_2$O-n-butyl B=carbamoyloxy | 0.6 | 97.7° | 53.78 | 53.74 | 7.56 | 7.61 | 11.76 | 11.94 |
| n-propyl n-propyl | A=—CH$_2$O-n-butyl B-carbamoyloxy | 0.45 | 105° | 56.13 | 56.01 | 8.05 | 8.30 | 10.90 | 10.76 |
| Allyl | A=—CH$_2$O-n-butyl | 0.67 | 64.1° | 56.69 | 56.81 | 7.08 | 7.31 | 11.02 | 10.90 |

Table 2-continued

| | Compounds of formula (III) in which | | | | | | | |
|---|---|---|---|---|---|---|---|---|
| | | $R_f$ | | C% | | H% | | N% |
| $R_5$-$R_6$ | $R_1$ | value | M.Pt.° C. | Cald. | Found | Cald. | Found | Cald. | Found |
| Allyl Ethyl | B-carbamoyloxy A=—$CH_2$O-n-butyl | 0.50 | 70.8° | 57.14 | 57.51 | 8.27 | 8.52 | 10.52 | 10.42 |
| iso-amyl Ethyl | B-carbamoyloxy A=—$CH_2$O-n-butyl | 0.43 | 93.6° | 63.00 | 62.92 | 7.18 | 7.40 | 7.73 | 7.53 |
| Phenyl Ethyl | B-OH A=—$CH_2$-O-$CH_3$ | 0.24 | 161.6° | 56.19 | 56.13 | 5.78 | 6.00 | 11.57 | 11.46 |
| Phenyl Ethyl | B=carbamoyloxy A=—$CH_2$-O-$C_2H_5$ | 0.27 | 162.6° | 57.29 | 57.20 | 6.70 | 6.87 | 11.14 | 11.26 |
| Phenyl Ethyl | B-carbamoyloxy A=—$CH_2$-O-n . $C_3H_7$ | 0.57 | 105° | 58.20 | 58.26 | 6.32 | 6.49 | 10.74 | 10.80 |
| Phenyl Ethyl | B-carbamoyloxy A=—$CH_2$-O-n . $C_4H_9$ | 0.45 | 120° | 59.25 | 59.34 | 6.67 | 6.70 | 10.37 | 10.46 |
| Phenyl Ethyl | B=carbamoyloxy A=—$CH_2$O-isopropyl | 0.45 | 102° | 58.20 | 58.44 | 6.32 | 6.38 | 10.74 | 10.37 |
| Phenyl | B=carbamoyloxy | | | | | | | | |

In the above two tables, the $R_f$ value refers to t.l.c. on silica gel using 20:40 parts acetonitrile to benzene. Table 3 shows the complexes that we have prepared, all of which are novel in the pure form and may be prepared by one or other of the methods illustrated above.

TABLE 3

| | | | | | | | C% | | H% | | N% | |
|---|---|---|---|---|---|---|---|---|---|---|---|---|
| | $R_1$  $R_2$ | $R_3$  $R_4$ | $R_5$  $R_6$ | $R_7$  $R_8$ | M.Pt°C. | Cald. | Found | Cald. | Found | Cald. | Found. |
| (1) | A=—$CH_2$-O-n,$C_4H_9$ B=carbamoyloxy | Ethyl | Ethyl | Ethyl | Glass | 53.78 | 53.63 | 7.56 | 7.57 | 11.76 | 11.64 |
| (2) | " | n-propyl | n-propyl | n-propyl | Glass | 56.10 | 56.30 | 8.05 | 8.15 | 10.90 | 10.75 |
| (3) | " | Allyl | Allyl | Allyl | Glass | 56.60 | 56.64 | 7.08 | 7.30 | 11.01 | 10.74 |
| (4) | " | Ethyl iso-amyl | Ethyl iso-amyl | Ethyl iso-amyl | Glass | 57.14 | 57.60 | 8.27 | 8.49 | 10.58 | 10.27 |
| (5) | " | Ethyl Phenyl | Ethyl Phenyl | Ethyl Phenyl | 50.6° | 59.30 | 59.39 | 6.67 | 6.75 | 10.37 | 10.35 |
| (6) | " | Ethyl | Ethyl | Ethyl | 39.8° | 58.01 | 58.20 | 6.87 | 7.09 | 10.68 | 10.69 |
| (7) | " | Phenyl Allyl | Phenyl Ethyl | Phenyl Ethyl | 45.2° | 58.64 | 58.60 | 6.76 | 6.72 | 10.51 | 10.49 |
| (8) | A=—$CH_2$-O-$C_2H_5$ B=carbamoyloxy | Phenyl Ethyl Phenyl | Phenyl Ethyl Phenyl | Phenyl Ethyl Phenyl | 138.1° | 57.29 | 57.20 | 6.10 | 6.20 | 11.14 | 10.92 |
| (9) | A=$CH_2$-O-n-$C_3H_7$ B=carbamoyloxy | Ethyl Phenyl | Ethyl Phenyl | Ethyl Phenyl | 40.8° | 58.20 | 58.16 | 6.32 | 6.46 | 10.74 | 10.33 |
| (10) | A=—$CH_2$-O-n-$C_4H_9$ B=OH | Ethyl Phenyl | Ethyl Phenyl | Ethyl Phenyl | Glass | 63.00 | 62.95 | 7.18 | 7.35 | 7.73 | 7.59 |
| (11) | A=—$CH_2$-O-isopropyl B=carbamoyloxy | Ethyl Phenyl | Ethyl Phenyl | Ethyl Phenyl | 56.6° | 58.2 | 58.3 | 6.32 | 6.41 | 10.74 | 10.64 |
| (12) | A=—$CH_2$-O-$^n$amyl B=-carbamoyloxy | Ethyl Phenyl | Ethyl Phenyl | Ethyl Phenyl | 60.1° | 60.14 | 60.10 | 6.92 | 7.03 | 10.02 | 9.94 |

These complexes are considered all to be novel since they are free both from uncombined malonylurea material or from undesirable degradation products, unlike two compositions of similar material involving phenobarbital and veronal in our earlier British Pat. No. 1,193,438.

Evidence of complex formation is provided by a study of the absorption spectra of the individual molecules that form the complex, and the complex itself. Thus, in relation to complex No. 5 and the constituents of it, the compound of formula II in which $R_3$ and $R_4$ are ethyl and phenyl shows an important peak at 830–840 cm$^{-1}$ in the infra-red spectrum and this peak is completely absent in the IR spectrum of the complex. Similarly, for the same constituent, an important peak at 1770 cm$^{-1}$ is completely absent in the IR spectrum of the complex. It is notable that this peak is, however, exhibited by a simple mixture of the three constituents. The constituent of complex No. 5, of formula IV in which $R_7$ and $R_8$ represent ethyl and phenyl groups and $R_2$ is a group in which A is —$CH_2O^n$ butyl and B is carbamoyloxy, shows a peak at 1615 cm$^{-1}$ which disappears completely in the IR spectrum of the complex.

The pharmacological effects of the complexes may be studied by reference to the most fully researched of them, complexes Nos. 5 & 11 in Table 2, wherein for $R_1$ and $R_2$, which are identical, A is —$CH_2O^n$ butyl or isopropyl, B is a carbamoyloxy group and $R_3$ and $R_4$, $R_5$ and $R_6$, and $R_7$ and $R_8$ are respectively ethyl and phenyl groups. The nucleus of these complexes is thus the phenobarbital nucleus.

Tests on the rat and guinea pig have demonstrated that the complexes exhibit a considerably modified hypnotic power and toxicity when compared with the properties of their constituents. Using comparative tests made on the basis of total quantity of constitutent either combined in the complexes or as an individual compound, the results have been remarkable. Except in very high doses for example, the complexes do not induce coma at all readily, in itself a remarkable fact when compared to both the action of phenobarbital in the same, but uncombined amount and a mixture of phenobarbital and the di-N,N-substituted constituent of the complexes. Likewise, up to quite heavy dosage levels, the muscular tone of the animal is maintained when the complexes are administered, in complete contrast to the administration of individual N-unsubstituted barbiturate when complete coma and flaccidity result.

It is difficult to test anti-tremor effects pharmacologically since no compound as yet administered to animals is capable of inducing a tremor response of the type shown by humans suffering from alcoholism. However, clinical trials have indicated that the complexes have tremendous potential as tranquillisers in antitremor use, particularly as the consciousness of the patient appears unimpaired and the risk of addiction is minimal. Thus, the complexes are of considerable value in the treatment of alcoholism.

The complexes of the invention may be administered either on their own or in compositions. The compositions may take the form of tablets, coated tablets, capsules, lozenges, ampoules for injection, solutions, etc.

The carriers or excipients in such compositions may, for example, be those conventional for such forms and may include starch, lactose, magnesium stearate, talc, gelatin, sterile pyrogen-free water, or suspending, emulsifying, dispersing, thickening or flavouring agents.

Dosage unit forms such as tablets, capsules or ampoules are preferred, and each unit contains 50 to 500 mg. of active substances, preferably 100 to 300 mg.

The complexes of the invention are prepared from their individual constituents and the preparation of some of these is outlined below. All of the compounds described in Tables 1 and 2 were prepared by the methods described below.

PREPARATION 1

5,5-Diallyl-N-(3'-$n$ butoxy-2'-carbamoyloxypropyl) malonylurea and 5,5-diallyl-N,N'-di-(3'-$n$ butoxy-2'-carbamoyloxypropyl) malonylurea 23 g of sodium 5,5-diallylmalonylurea and 21 g of 1-chloro-3-butoxypropan-3-ol carbamate are mixed in a flask equipped with a stirrer and reflux condenser. The mixture is heateed, with stirring, for 10 hours at from 100° to 110° C.

(a) The resulting mass is extracted with water and toluene and the two layers are separated. The toluene layer is washed several times with 1 N. NaOH and then with distilled water. The resulting solution is dried over anhydrous sodium sulphate, and then filtered and concentrated to half its original volume. An equivalent amount of petroleum ether is added and an oily mass of 5,5-diallyl-N,N'-di(3'-$n$ butoxy-2'-carbamoyloxypropyl) malonylurea is obtained. This oily mass is purified by successive dissolutions in ether and chloroform, precipitating the compound with petroleum ether or an aliphatic hydrocarbon e.g. heptane or cyclohexane. The last traces of solvent are removed by evaporation under reduced pressure and 5,5-diallyl-N,N'-di(3'-$n$ butoxy-2'-carbamoyloxypropyl) malonylurea is left as a pale yellow vitreous mass.

(b) 5,5-Diallyl-N-(3'-butoxy-2'-carbamoyloxypropyl) malonylurea is prepared from the aqueous extract of the reaction product mixture and the alkaline washings of the toluenic extract above. The combined extracts are treated with a 10% hydrochloric acid solution until precipitation is complete. The precipitate is a pasty mass containing unchanged starting material and mono-N-substituted product. The mass is dissolved in ether and extracted several times with a solution of sodium carbonate in which the starting material is much the more soluble. The remaining ether solution is washed with distilled water until it is neutral and is then dried over anhydrous sodium sulphate, filtered and the filtrate concentrated. On adding petroleum ether, the product precipitates as a paste that hardens in time. The resulting amorphous powder may be crystallised from alcohols or by other conventional methods. Melting point of the recrystallised white powder=64.1° C.

Preparation 2

5-Ethyl-5-phenyl-N-3'-$n$ butoxy-2'-hydroxypropyl) malonylurea and 5-ethyl-5-phenyl-N,N'-di-(3'-$n$ butoxy-2'-hydroxypropyl) malonylurea 25.4 g of sodium phenobarbital and 150 g of chlorobutoxypropanol are introduced into a flask equipped with a stirrer and reflux condenser. The mixture is heated while stirring between 110° and 120° C. for 4 hours. The product mixture is allowed to cool and the sodium chloride formed is filtered off. The filtrate is distilled off at reduced pressure and the residue is a resinous product having a yellowish colour. This is dissolved in toluene and washed with 1 N. NaOH. The procedures followed are then identical to those in Preparation 1. The resulting N-monosubstituted product obtained from the alkaline extractions may be crystallised by conventional means, e.g. from a mixture of chloroform/petroleum ether and the final product is a white powder of melting point 93.6° C.

From the toluenic solution itself the N,N'-di-substituted product is obtained by repeated precipitations with petroleum ether. The product is a glass.

PREPARATION 3

5-Ethyl-5-phenyl-N-(3'-$n$ propyloxy-2'-carbamoyloxypropyl) malonylurea and 5-ethyl-5-phenyl-N,N'-di-(3'-$n$ propyloxy-2'carbamoyloxypropyl) malonylurea 25.4 g of sodium phenobarbital and 19.5 g of 1-chloro-3-propyloxy propan-3-ol carbamate are mixed with 30 ml dry toluene. The mixture is heated under reflux, stirring well, for 10 hours. A further 100 ml of toluene is then added and the mixture is extracted several times with 1 N. NaOH. The procedure followed is then identical to Preparation 1.

5-Ethyl-5-Phenyl-N-(3'-$n$ propyloxy-2'-carbamoyloxypropyl) malonylurea is obtained as a white powder, melting point 132° C., and 5-ethyl-5-phenyl-N,N'-di(3'-$n$ propyl-2'-carbamoyloxypropyl) malonylurea is obtained as a clear yellow glass, m.pt. 35.2° C., from the toluenic solution by repeated precipitation with petroleum ether.

PREPARATION 4

5,5-Diethyl-N-(3'-n-butoxy-2'-carbamoyloxypropyl) malonylurea and 5,5-diethyl-N,N'-di(3'-n-butoxy-2'-carbamoyloxypropyl) malonylurea An alcoholic solution of sodium barbital is prepared by adding 2.3 g of metallic sodium to 100 ml absolute ethanol and then adding to the resulting solution 18.5 g of barbital with agitation for 30 min. at room temperature. 21 g of 1-chloro-3-butoxypropan-3-ol carbamate are added and the mixture is heated with good stirring under reflux for 36 hours. The mixture is allowed to cool, the sodium chloride is filtered off and the alcohol is evaporated off under reduced pressure. The residue is a yellowish resinous mass, which is then dissolved in ether and extracted several times with 1 N. NaOH. The procedure is then essentially identical to that in Preparation 1.

5,5-Diethyl-N-(3'-$n$ butoxy-2'-carbamoyloxypropyl) malonylurea is a white powder with a melting point of 97.7° C.

5,5-Diethyl-N,N'-di(3'-$n$ butoxy-2'-carbamoyloxypropyl) malonylurea is obtained by repeated precipitation from the ether solutions and forms a light yellow coloured glass, m.pt 50.8° C.

PREPARATION 5

5-Ethyl-5-phenyl-N(3'-isopropyloxy-2'-carbamoyloxypropyl) malonylurea and 5-ethyl-5-phenyl-N,N'-di(3'-isopropyloxy-2'-carbamoyloxypropyl) malonylurea 200 g of 1-chloro-3-isopropyloxypropan-1-ol carbamate and 254 g of dry sodium phenobarbital are mixed. The mixture is heated in an oil bath stirring well. The temperature of the mixture is raised to between 100° and 150° C. and is maintained for 8 hours.

500 ml of toluene and 250 ml of water are added to the molten mixture and the two ensuing layers are separated. The toluenic layer is extracted twice with 400 ml of a 3% solution of caustic soda. The solution is then washed with water up to neutral pH.

5-Ethyl-5-phenyl-N-(3'-isopropyloxy-2'-carbamoyloxypropyl) malonyl urea is obtained by fractional precipitation of the solution of caustic soda using hydrochloric acid. The desired product precipitates first, followed by a mixture of phenobarbital and product. The product may be recrystallised from toluene. The product comprises small brilliant white crystals, m.pt 102° C.

The 5-ethyl-5-phenyl-N,N'-di(3'-isopropyloxy-2'-carbamoyloxypropyl) malonylurea is extracted from the toluenic solution by concentrating it to half its original volume and letting it rest at room temperature. The crystals are filtered and recrystallised twice from alcohol. White crystals, m.pt 147.1° C., are obtained.

The preparation of complexes of the invention is described in the following Examples which should not be interpreted as limiting the invention:

EXAMPLE 1

Preparation of Complex No. 11 described above

Phenobarbital, 5-ethyl-5-phenyl-N-(3'-isopropyloxy-2' carbamoyloxypropyl) malonylurea and 5-ethyl-5-phenyl-N,N'-di(3'-isopropyloxy-2' carbamoyloxypropyl) malonylurea are mixed in a mortar in a molar proportion of 1:2:1 respectively. The mixture is then heated up to complete fusion and then poured into cold water. The solid masses are broken up to form a powder which is filtered. The residue is washed several times with water. The powder is dried to constant weight in a vacuum desiccator over phosphorus pentoxide. The powder has a melting point of 56.6° C.

EXAMPLE 2

Preparation of Complex No. 7 as indicated above 5,5-Diallylmalonylurea, 5-ethyl-5-phenyl-N-(3'-$n$ butoxy-2'-carbamoyloxypropyl) malonylurea and 5-ethyl-5-phenyl-N,N'-di(3'-$n$ butoxy-2'-carbamoyloxypropyl) malonylurea, in molar quantities of 1:2:1 respectively, are dissolved with heating in the minimum quantity of ethanol. The solution is allowed to cool and twice its volume of water is added. The paste formed is separated from the liquid and washed with hot water. The mixture is allowed to cool and the two layers are separated. The solid is then washed several times with cold water. The mass is sufficiently hard at this point to be dried to constant weight to a desiccator and pulverised. Melting point 45.2° C.

EXAMPLE 3

Preparation of Complex No. 5 as described above

Phenobarbital, 5-ethyl-5-phenyl-N-(3'-n-butoxy-2'-carbamoyloxypropyl) malonylurea and 5-ethyl-5-phenyl-N,N'-di(3'-n-butoxy-2'-carbamoyloxypropyl) malonylurea are mixed in a mortar in a molar proportion of 1:2:1 respectively. The mixture is then heated up to complete fusion and then poured into cold water. The solid masses are broken up to form a powder which is filtered. The residue is washed several times with water. The powder is dried to constant weight in a vacuum desiccator over phosphorus pentoxide. The powder has a melting point of 50.6° C.

The remaining complexes described in Table 2 may be prepared in a fashion analogous to those of the above Examples.

We claim:

1. A tranquillising complex exhibiting anti-tremor activity of the structure (I)

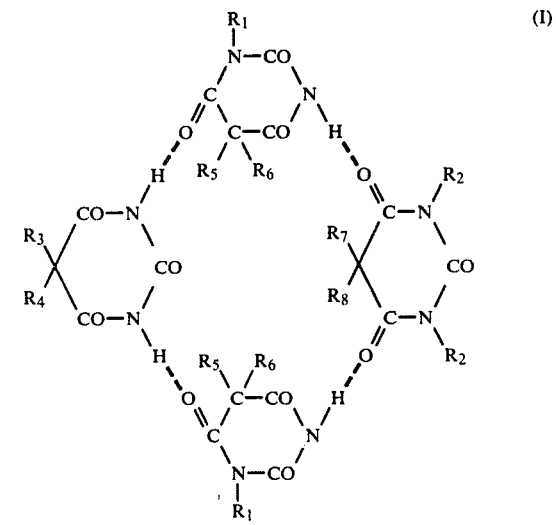

wherein $R_1$ and $R_2$, which are the same or different, each represent a group of the formula —$CH_2CHAB$, in which A is a hydrogen atom and B a hydroxyl group; or A is a group of the formula $-CH_2OX$ wherein X is a hydrogen atom or $C_{1-5}$ alkyl, and B is a group of the formula $-OY$ wherein Y is a hydrogen atom or carbamoyl or carboalkoxy, and $R_3$, $R_4$, $R_5$, $R_6$, $R_7$ and $R_8$, which are the same or different, each represent a hydrogen atom, $C_{2-5}$ alkyl or alkenyl, or phenyl, the dotted lines representing hydrogen bonding.

2. A complex as claimed in claim 1 in which A represents a group $-CH_2OX$ wherein X is $C_{1-4}$ alkyl and B is carbamoyloxy.

3. A complex as claimed in claim 1 wherein A represents group $-CH_2OX$ wherein X is isopropyl or n-butyl, B is carbamoyloxy and $R_3$ to $R_8$ are each selected from the group consisting of ethyl, allyl, isoamyl and phenyl.

4. The complex of claim 1 wherein $R_1$ and $R_2$ each represent the group $-CH_2CH(O.CONH_2).CH_2O-n-C_4H_9$, $R_3$, $R_5$ and $R_7$ each represent ethyl and $R_4$, $R_6$ and $R_8$ each represent phenyl.

5. A complex as claimed in claim 1 substantially free from any uncombined N,N-unsubstituted malonylurea.

6. A pharmaceutical composition comprising an effective amount of a complex of structure (I) as claimed in claim 1 together with a pharmaceutical carrier, diluent or excipient.

7. A composition as claimed in claim 6 in dosage unit form, each unit containing 50 to 500 mg of the complex.

8. A composition as claimed in claim 6 which contains the complex as claimed in claim 5.

9. A process for the preparation of a complex of structure (I) as claimed in claim 1 which comprises either dissolving or fusing together in a molar ratio of 1:2:1 a malonylurea derivative of formula (II)

$$\begin{array}{c} R_3 \\ R_4 \end{array} \diagdown \begin{array}{c} CO-NH \\ \\ CO-NH \end{array} \diagup CO \quad \text{(II)}$$

an N-substituted malonylurea derivative of formula (III)

$$\begin{array}{c} R_5 \\ R_6 \end{array} \diagdown \begin{array}{c} CO-N \diagup R_1 \\ \\ CO-N \diagdown H \end{array} \diagup CO \quad \text{(III)}$$

and an N,N-disubstituted malonylurea derivative of formula (IV)

$$\begin{array}{c} R_7 \\ R_8 \end{array} \diagdown \begin{array}{c} CO-N \diagup R_2 \\ \\ CO-N \diagdown R_2 \end{array} \diagup CO \quad \text{(IV)}$$

wherein $R_1$, $R_2$, $R_3$, $R_4$, $R_5$, $R_6$, $R_7$ and $R_8$ are as defined in claim 1 followed by treatment of the reaction mixture with water and isolation of the complex.

10. A process as claimed in claim 9 wherein the compounds of formulae (II) (III) and (IV) are fused, the resulting reaction mixture is treated with cold water, dried and pulverised.

11. A process as claimed in claim 9 wherein the compounds of formulae (II), (III) and (IV) are dissolved in alcohol, the resulting reaction mixture is cooled and treated with water to produce an oil which is washed with warm water, dried and the resulting product pulverised.

12. A method of treating alcoholism which comprises administering to a human subject therapeutically an effective quantity of a complex as claimed in claim 1.

* * * * *